United States Patent [19]

Steinman

[11] Patent Number: 4,812,400
[45] Date of Patent: Mar. 14, 1989

[54] PROCESS FOR MEASURING SODIUM LEVELS IN BIOLOGICAL FLUIDS

[76] Inventor: Gary D. Steinman, 150-38 Union Turnpike, Apt. 1-0, Flushing, N.Y. 11367

[21] Appl. No.: 885,412

[22] Filed: Jul. 14, 1986

[51] Int. Cl.$^4$ .................. C12Q 1/42; C12Q 1/00; C12Q 1/34; C12Q 1/48
[52] U.S. Cl. .......................................... 435/21; 435/4; 435/18; 435/15; 435/25; 435/805; 435/810
[58] Field of Search ............... 435/4, 21, 18, 805, 435/810, 15, 25; 427/2

[56] References Cited

U.S. PATENT DOCUMENTS

| | | |
|---|---|---|
| 4,071,413 | 1/1978 | Takahashi et al. ............... 435/15 X |
| 4,246,342 | 1/1981 | Misaki et al. .................... 435/25 |
| 4,476,222 | 10/1984 | Ohtani et al. .................... 435/14 |
| 4,490,465 | 12/1984 | Limbach et al. ................. 435/14 |
| 4,657,854 | 4/1987 | Wegfahrt, Jr. .................... 435/14 |

OTHER PUBLICATIONS

Kumar, A., "Spectrophotometric Assay of Na and K: An Emerging Technology in Blood Electrolyte Analysis", *American Clinical Laboratory*, vol 7, No. 5, pp. 22–27, (1988).
Skou, J. "Chem Abstracts," vol. 55, (1961), 646i.
Josephson, L., and L. Cantly, (1977), Biochemistry, vol. 16, No. 21, 4572–4578.

*Primary Examiner*—Robert J. Warden
*Assistant Examiner*—Toni R. Scheiner
*Attorney, Agent, or Firm*—Michael I. Kroll

[57] ABSTRACT

A process for measuring the sodium concentration of a biological fluid, such as blood serum or urine, is carried out by fixing the amounts of adenosine-5'-triphosphate (ATP), adenosine triphosphatase (ATPase), magnesium, and potassium, in the presence of a buffer, in enzymatic Reaction I,

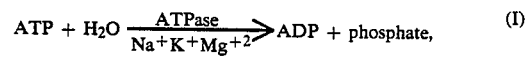

$$ATP + H_2O \xrightarrow[Na^+ K^+ Mg^{+2}]{ATPase} ADP + phosphate, \quad (I)$$

where ADP is adenosine diphosphate, and measuring the rate of appearance of the products so that the rate of reaction of adenosine triphosphatase can be determined. The reaction rate of this enzyme is directly proportional to the level of sodium present. The sodium concentration of the biological fluid being tested is quantitatively determined by comparing the reaction rate of adenosine triphosphatase to a standard known sodium concentration. Preferably, the reaction rate of adenosine triphosphatase is measured by reacting the ADP product with phosphoenolpyruvate under the catalysis of pyruvate kinase and measuring the pyruvate product of this second reaction. Quantitation of the pyruvate produced determines the activity of adenosine triphosphatase in Reaction I, which is directly proportional to the sodium concentration in the biological fluid being tested. Colorimetric standards of known sodium concentration are used as points of reference. A paper phase procedure for determining sodium levels in biological fluids is also provided.

11 Claims, No Drawings

PROCESS FOR MEASURING SODIUM LEVELS IN BIOLOGICAL FLUIDS

This invention relates to a chemical process for the measurement of sodium in biological fluids, such as urine or blood. More particularly, it relates to an enzyme reaction that is sodium-activated in a specific quantitative fashion.

The importance of being able to accurately measure levels of sodium is well known. Sodium maintains the body's internal water balance and is essential for proper muscle contraction and nerve conduction. The kidney is the primary organ controlling the level of sodium. Significant deviations are often seen in cases of dehydration due to fever, diarrhea, vomiting and extreme heat exposure. Hormone disorders, kidney and heart disease, and high blood pressure are all affected by and in turn act on the blood sodium level. A test for sodium is often ordered to monitor patients with hypertension being treated with diuretics.

The most common techniques employed today for measuring sodium in biological fluids are emission flame photometry, atomic absorption spectrophotometry, and ion-selective electrode potentiometry. These methods require sophisticated analytical equipment, precise manipulation, and technical expertise. A critical need exists for a simple, accurate and inexpensive method applicable for use in the physician's office or even within a patient's home to specifically determine sodium levels in biological systems.

Accordingly, it is an object of the present invention to provide an accurate, yet inexpensive, method to determine sodium levels in biological fluids. An invention to provide such a method should be executed in a paper-phase procedure, which is particularly economical since the use of minute amounts of premeasured reagents is possible, as well as in the solution phase. A further object of the invention is to provide a method that may be readily adaptable to existing and widely available instrumentation, thereby further allowing for economical and convenient use.

Certain of the foregoing and related objectives are readily attained by utilizing the sodium dependence of adenosine triphosphatase (EC 3.6.1.3). While the chemistry of this enzyme is known, there appears to have been no attempt to utilize its sodium stimulation in a quantitative analytical fashion, let alone employ this property to measure sodium levels in biological systems. (J. C. Skou, Biochim. Biophy. Acta, 23, 394 (1957).) It has been the general practice of biochemists to add excess sodium to systems designed to evaluate and utilize adenosine triphosphatase from various sources. (e.g., L. Josephson. and L. C. Cantley, Biochem., 16, 4572 (1977).) Thus, the prior art, by directing the use of saturating amounts of sodium, teaches away from the methodology of the present invention. Furthermore, in the 30 years since the original observation, no apparent attempt has been made to apply such a principle in the quantitative determination of sodium in biological systems. (N. W. Tietz, ed., "Textbook of Clinical Chemistry", W. B. Saunders, Philadelphia, 1986, p. 1174.)

Adenosine triphosphatase (ATPase) cleaves the terminal phosphate off adenosine-5'-triphosphate (ATP) to yield adenosine diphosphate (ADP) and inorganic phosphate (Pi).

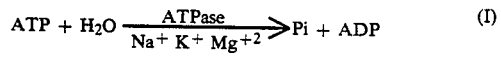

$$ATP + H_2O \xrightarrow[Na^+ \; K^+ \; Mg^{+2}]{ATPase} Pi + ADP \quad (I)$$

The phosphatase activity is greatest between pH 7.2 and 8.0 with enzyme from various sources. The equilibrium of the hydrolytic reaction using this enzyme is shifted toward the two products in the presence of magnesium, potassium, and sodium. In its natural setting, the enzyme is membrane-bound and is responsible for energizing the exchange of sodium and potassium across membranes. By using in vitro a predetermined amount of ATPase, ATP, $K^+$, and $Mg^{+2}$, and measuring by some means the appearance of products, one may determine the degree of activation of ATPase, the enzyme catalyst. The extent of reaction, i.e., the activity of this enzyme, is directly proportional to the sodium concentration.

The phosphate product can be measured by the well known method of Fiske and Subbarow. Similarly, techniques which measure the appearance of ADP can be applied for determining the rate of ATPase activity. The ADP product of Reaction I can react with phosphoenolpyruvate (PEP), in the presence of pyruvate kinase (PK), to yield pyruvate, as in Reaction II.

$$ADP + PEP \xrightarrow[K^+ \; Mg^{+2}]{PK} ATP + pyruvate \quad (II)$$

Finally, as described in U.S. patent application Ser. No. 06/729,633, a number of methods can be used to measure the amount of pyruvate product. The pyruvate can be reacted with lactate dehydrogenase and reduced nicotinamide adenine dinucleotide, with the change in the amount of the latter being followed in an ultraviolet spectrophotometer. Alternatively, reaction with pyruvate oxidase can yield peroxide; when coupled with peroxidase and added indicator, the degree of color change is proportional to the amount of pyruvate present.

Another mode for quantitatively determining the pyruvate product of Reaction II is to react it with 2,4-nitrophenylhydrazine. After adding dilute alkali, the visible color produced is proportional to the quantity of pyruvate, which, in turn, is a measure of the activity of the ATPase in Reaction I. As noted in the abovementioned patent application, these quantitative reactions can be carried out in solution or in the "paper" phase, the latter being especially economical and practicable for in-home or in-office use. In solution phase, the final optical density of the solution is, preferably, measured in a spectrophotometer. For use in the paper phase, the reagent strips are prepared so that the color produced can be measured by eye with reference to a standard color chart or in a relectance spectrophotometer.

Thus, in summary, under the stimulation of sodium, adenosine triphosphotase catalyzes the hydrolysis of ATP to ADP (Reaction I). The diphosphate product then reacts with phosphoenolpyruvate, by the mediation of pyruvate kinase, to yield pyruvate (Reaction II). The amount of pyruvate is measured and is directly proportional to the quantity of sodium present in the original test sample.

In the following, an example of a typical format which can be used to measure the sodium concentration of test samples will be more fully described. However, it should be noted that this sample is given only by way of illustration and not limitation. While only one embodiment and example of typical solutions of the present invention are shown and described, it is obvious that many changes and modifications may be made thereunto without departing from the spirit and scope of the invention.

EXAMPLE

First, a reagent solution comprising 100 units pyruvate kinase, 2 mg KCl, 10 mg Mg ATP, and 3 mg PEP in 1.05 ml of 0.2M Tris/0.05M $Mg^{+2}$ buffer of pH 7.5 is prepared. An enzyme suspension of 5 units ATPase (an insoluble sodium iodide extracted fraction containing 10% protein, 90% sucrose, 0.4% Na EDTA, and 0.06% NaCl) in 2.5 ml Tris/Mg buffer is also prepared. To 0.05 ml of test sample are added 0.10 ml reagent solution and 0.05 ml enzyme suspension. After 4 minutes incubation at room temperature, 0.3 ml 2,4-D (20 mg 2.4-dinitrophenylhydrazine in 1N HCl) is added. This is followed by incubation at room temperature for another 3 minutes and then the addition of 3 ml of 0.4N NaOH. After 1 minute, the optical density is read with a spectrophotometer at 500 nm and compared against a known standard, thereby determining the sodium concentration of the sample being tested.

What is claimed is:

1. A process for measuring the sodium concentration of a biological fluid, comprising the steps of:
   (a) supplying predetermined amounts of adenosine-5'-triphosphate (ATP), adenosine triphosphatase (ATPase), magnesium, and potassium in the presence of a buffer in a reaction mixture for enzymatic Reaction I,

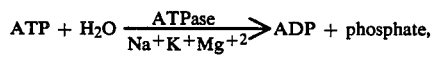

where ADP is adenosine diphosphate and where the reactants and containers used to carry out the process are of known initial sodium content;
   (b) adding a biological fluid test sample and then measuring the rate of appearance of the products in Reaction I so that the reaction rate of adenosine triphosphatase, being proportional to the concentration of sodium, is determined;
   (c) comparing the reaction rate of adenosine triphosphatase in Reaction I against the reaction rate of the same in one standard of known sodium concentration (in the range 130-150 mEq/L; and
   (d) then determining the sodium concentration of said biological fluid.

2. The process according to claim 1, wherein said buffer employed is the Tris buffer, said buffer being 0.2M Tris and 0.05M $Mg^{+2}$ with pH of 7.5.

3. The process according to claim 1, wherein steps (b) and (c) are carried out by comparison of the optical density of the visible color produced in coupled Reactions II and III,

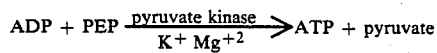

where PEP is phosphoenolpyruvate and 2,4-D is 2,4-dinitrophenylhydrazine, against at least one colorimetric standard of known sodium concentration in the range 130-150 mEq/L, the optical density of the visible color produced, as a function of time, being directly proportional with the sodium concentration of said biological fluid.

4. The process according to claim 1, wherein the ADP product from Reaction I is measured using coupled Reactions II, IV, and V,

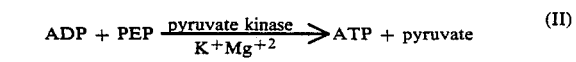

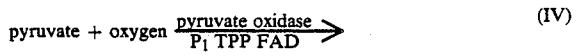

$$CH_3COO-H_2PO_3 + H_2O_2$$

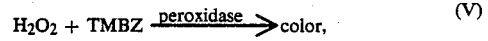

where TPP is thiamine pyrophosphate, FAD is flavin adenine dinucleotide, Pi is inorganic phosphate, and TMBZ is tetramethylbenzidine, in a spectrophotometer against at least one analytical standard of known concentration (in the range 130-150 Na mEq/L, the optical density of the produced color, as a function of time, being directly proportional with the sodium concentration of said biological fluid.

5. The process according to claim 1, wherein the ADP product from Reaction I is measured using coupled Reaction VI,

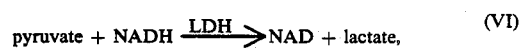

where NAD is nicotinamide adenine dinucleotide, LDH is lactate dehydrogenase, and NADH is reduced NAD, in a spectrophotometer against at least one analytical standard of known concentration (corresponding to the range 130-150 Na mEq/L, the optical density of the produced color, as a function of time, being inversely proportional with the sodium concentration of said biological fluid.

6. The process according to claim 1, wherein said biological fluid being tested is whole blood, blood serum, blood plasma, urine, saliva, cerebrospinal fluid, sweat, stool extract, tears, or peritoneal fluid.

7. The process according to claim 3, wherein the optical density is measured by reflectance or transmission spectrophotometry.

8. The process according to claim 3, wherein the resultant color is evaluated by comparison with a standardized color chart whose selected shades and intensities correspond to particular concentrations of sodium when measured by the system employing Reactions I, II, and III.

9. A process for making a reaction mixture for measuring the sodium concentration of a biological fluid, such as whole blood, urine, blood serum, or blood plasma, comprising the step of:
   supplying predetermined amounts of adenosine-5'-trisphosphate, adenosine triphosphatase, magnesium, and potassium in the presence of a buffer in a reaction mixture for enzymatic Reaction I:

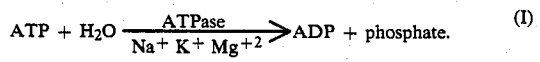

10. A process for making a bibulous material for measuring the sodium concentration of a biological fluid, such as whole blood, urine, blood serum, or blood plasma, for use in a dry chemistry procedure, comprising the steps of:

(a) supplying predetermined amounts of adenosine-5'-triphosphate, adenosine triphosphatase, a buffer, and potassium in aqueous solution;

(b) adding an indicator system consisting of predetermined amounts of inorganic phosphate, pyruvate oxidase, thiamine pyrophosphate, flavin adenine dinucleotide, peroxidase, and tetramethylbenzidine, for quantitative colorimetric analysis to said aqueous solution prepared as in step (a);

(c) dipping a bibulous material of paper, of a cellulose derivative, or of a synthetic material into said resultant solution prepared as in step (b);

(d) removing said bibulous material from said aqueous solution;

(e) air-drying said treated bibulous material;

(f) dipping said bibulous material into an organic solution of predetermined magnesium concentration also containing a cellulosed derivative;

(g) removing said bibulous material from said organic solution;

(h) air-drying said bibulous material;

(i) applying said biological fluid to be tested to said impregnated bibulous material to initiate enzymatic Reaction I,

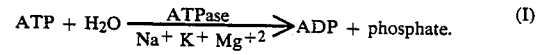

$$ATP + H_2O \xrightarrow[Na^+ \ K^+ \ Mg^{+2}]{ATPase} ADP + phosphate. \quad (I)$$

(j) measuring the rate of appearance of the products of the mixture by the quantity of color produced in the quantitative coupled colorimetric analysis using the indicator system added in step (b), by employing a reflectance spectrophotometer; and, (k) comparing the quantity of color produced by one analytical standard of known sodium concentration (in the range of 130–150 mEq/L, so that the quantity of color is directly proportional to the sodium concentration of said biological fluid being tested.

11. The process according to claim 10, wherein said organic solution of known magnesium concentration of step (f) comprises magnesium acetate dissolved in absolute methanol.

* * * * *